United States Patent [19]

Ventura

[11] Patent Number: 4,796,859
[45] Date of Patent: Jan. 10, 1989

[54] SLIT LAMP ASSEMBLY

[76] Inventor: Lori M. Ventura, 801 N. Venetian Dr., Apt. 1104, Miami, Fla. 33139

[21] Appl. No.: 144,306

[22] Filed: Jan. 14, 1988

[51] Int. Cl.$^4$ ............................ A61B 3/00; A61B 3/10
[52] U.S. Cl. ................................. 351/245; 351/214
[58] Field of Search ............... 351/200, 205, 222, 214, 351/244, 245; 350/321; 433/3; 604/322; 312/71; 211/59.3; 108/136; 221/279

[56] References Cited

U.S. PATENT DOCUMENTS 4,095,859  6/1978  Decker et al. .................. 351/245

Primary Examiner—Rodney B. Bovernick
Assistant Examiner—P. M. Dzierzynski
Attorney, Agent, or Firm—John Cyril Malloy

[57] ABSTRACT

An improved slit lamp assembly including a tonometer head adjustable height-wise with respect to a table included in the assembly and wherein a container is provided on the table with a supply of isopropyl alcohol impregnated swabs for use in disinfecting the tonometer head after use by each patient. The container includes an attachment structure for removably attaching it to the table so that when the supply of swabs is exhausted, a new supply may be placed in the container.

9 Claims, 1 Drawing Sheet

SLIT LAMP ASSEMBLY

FIELD OF THE INVENTION

This invention relates to slit lamp assemblies and more particularly to a slit lamp assembly which includes a tonometer head and carried on the assembly, a container with a supply of 70% isopropyl alcohol impregnated swabs.

BACKGROUND OF THE INVENTION

It is important to avoid community epidemics of ocular virus infections. In ophthalmology clinic settings, after use on each patient, there is a lack of uniformity in the handling of applanation tonometer heads of slip lamps commonly used in eye examinations. After use on a patient, some clinicians exchange one tonometer head for another, others wipe it with dry tissue, a finger or alcohol, and still others fail to make any effort to clean it. It has been learned that various viruses, including, especially, herpes simplex virus type I can be detected on innoculated tonometer heads for up to two hours during natural drying and, if the tonometer is kept moist, for more than eight hours. In the tears of patients there are other types of viruses, in addition to the herpes simplex virus type I, including that which causes adenovirus conjunctivitis or severe inflammation of the eyes. Because residual infectious virus, especially the herpes simplex virus type I, may remain on a dry-wiped tonometer head at levels capable of initiating infection and ocular disease if transferred from one patient to another, and, because the infectious virus may be transferred from the tonometer head to a dry-wipe or swab, possibly contaminating the fingers of an examiner, attention has been given to the problem of avoiding autoinoculation or infection of patients or examiners. Conscientious hand-washing procedures are helpful, but not always observed. Herpes simplex virus type I infectivity remains viable, even in the presence of many ophthalmic solutions. While the precise mechanism by which these solutions affect herpes simplex virus type I, it has been found that 10% Chlorox or a 70% isopropyl alcohol application were found to completely disinfect tonometer heads completely. In order to encourage that tonometer heads be disinfected after each use in order to avoid ocular transmission of virus infection, especially in cases of subclinical shedding of virus in tears as occurs with herpes simplex virus type I, adenoviruses, and human immunodeficiency viruses during eye examination, this invention provides in combination with a slit lamp assembly including a tonometer head, a container with a supply of 70% isopropyl alcohol swabs and means to mount it to the assembly.

OBJECTS OF THE INVENTION

It is, accordingly, an object of this invention to provide means for combatting any likelihood of a community epidemic of ocular virus infections and, more specifically, a slit lamp assembly including a container with a supply of 70% isopropyl alcohol swabs and means to mount the container to the assembly to promote disinfecting of tonometer heads after each use to avoid ocular transmission of virus infections.

It is another object of this invention to provide a simple and inexpensive means of avoiding such transmission of virus infection which is easy to install, may be conveniently utilized and which in general is for the purpose as set forth more fully herein.

In accordance with these and other objects which will become apparent hereinafter, the instant invention will now be described with reference to the accompanying drawings in which:

DESCRIPTION OF THE PREFERRED EMBODIMENT

Figure 1:
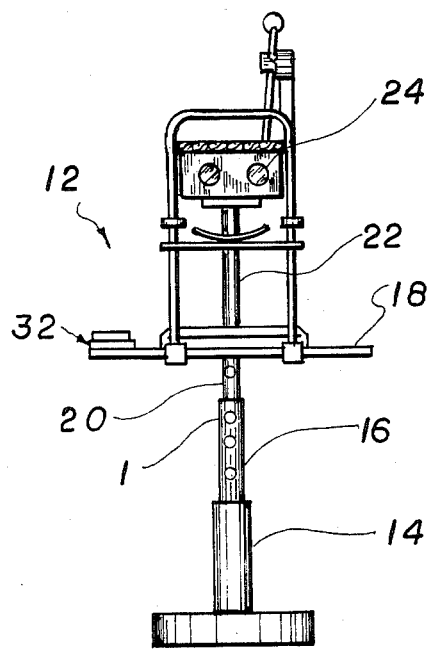
FIG. 1 is a front elevation view of an improved split lamp assembly.
Figure 2:
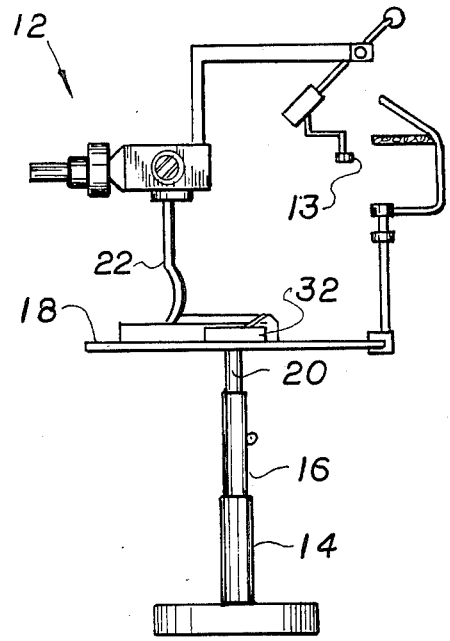
FIG. 2 is a side elevation view.
Figure 3:
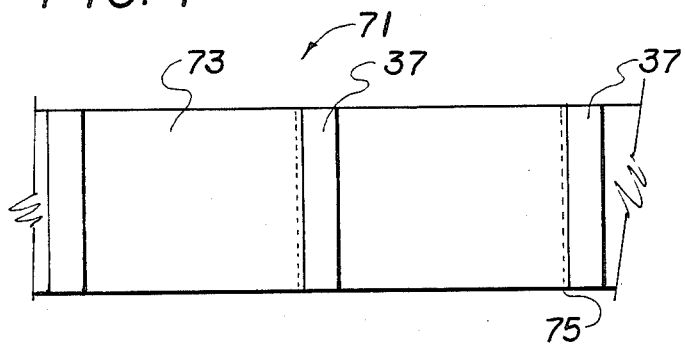
FIG. 3 is a partial view of a swab in accordance with this invention.
Figure 4:
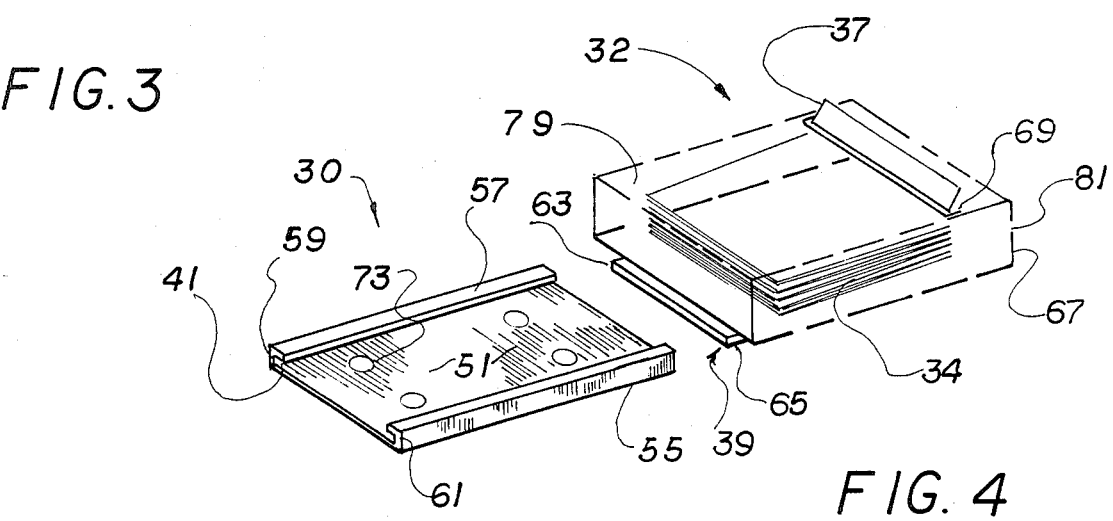
FIG. 4 is a view of the container seen in FIGS. 1 and 2 on the table of the split lamp assembly.

Referring to the drawings, a slit lamp assembly is generally indicated by the numeral 12. Generally speaking, it includes a stand 14 with an upstanding standard 16 and a table 18 on the stand. Conventionally, the standard includes means to adjust the table height, which may be pneumatic or, in a simple form, a pair of telescoping tubes indicated at 20 with a pin to maintain an adjusted height 13. In any event, means are provided to adjust the table height to accommodate the particular person whose eyes are being examined. The examination takes place by use of a device known as a slit lamp 22 including a tonometer head 13. It is carried on the table so that, as the adjustment of the height takes place, the portions 24 and 26 through which a person peers may be arranged at eye level. While a basic slip lamp assembly has been indicated in the drawings, there are numerous types of devices in the field which in general include the elements as set forth above.

In use, the apparatus is used repeatedly with different patients for examining their eyes and by so doing, the tonometer head is subjected to subclinical shedding of tears commonly recognized in persons infected with herpes simplex virus type I. It has been discovered that the herpes simplex virus type I virus is such that an infectious condition can be detected on experimentally inoculated tonometer heads for up to two hours during natural drying. Moreover, if tonometers were kept moist, the virus could be detected for eight hours. Various ophthalmic solutions including topical anaesthetics, dilating agents, and a fluorescein solution showed only minimal antiviral activity. It was further found that wiping a virus-infected tonometer head with a dry tissue was ineffective and allowed residual infectious virus to remain. It was discovered, however, that no infectious virus could be detected on infected tonometer heads that has been swabbed with 70% alcohol or Cholorox. To provide means to encourage routine swabbing of tonometer head with 70% isopropyl alcohol, after each patient examination to insure complete virus inactivation, the following structure in combination with a slit lamp assembly is described. Use of this structure and routine swabbing of tonometer heads prevents accidental transmission of virus in the eye examination process and avoids community epidemics of ocular virus infections. Thus, on the table 18, a mounting means 30 is provided for a container 32 in which there is a supply 34 of 70% isopropyl alcohol impregnated porous sheets each separated from one another by an antiwicking portion 37.

In the preferred embodiment, the container 32 is provided with companionate means 39 to interengage guide means 41 included in the mounting means so that the container may be positioned relative to the mounting means for convenient use following each eye examination. More specifically, while various embodiments are practical, the mount means may be a plate 51, screw connected through holes 53 to the table 18 and on which there are a pair of inturned flanges 55 and 57 on opposed guide walls 59 and 61. Also, the container 32 is provided on its lower surface with tracks 63 and 65 and a stop means 67 for ease of attachment and removal from the table by sliding movement of the container. The container which is preferably about 2"×2" is provided with a discharge mouth 69. Within the container a string 71 of the swabs 73 preferably 2"×2" are stacked and connected together at a perforated zone 75 so that for use the same may be removed one by one. Preferably, the perforated zone includes an antiwick portion 37.

In use after each eye examination, one of the swabs is removed from the container and the tonometer head is cleaned. The container lid 79 may be hingedly connected as at 81 so that an additional stack or supply of 70% isopropyl alcohol carrying swabs may be placed in the container.

While the instant invention has been shown and described in what is considered to be a practical and preferred embodiment, it is recognized that departures may be made therefrom within the spirit and scope of this invention which is, therefore, not to be limited except as set forth in the claims hereinafter and in accordance with the doctrine of equivalents.

What is claimed is:

1. For use after eye examinations, the combination of a slit lamp assembly including (a) a stand, (b) a table on the stand, (c) means to adjust the table height relative to the stand, and (d) a slit lamp including a tonometer head carried on the table, and
   a container having a swab discharge opening,
   means on the table to removably connect the container to the table, and
   a plurality of alcohol impregnated swabs in the container for withdrawal of the swabs through the opening for use to clean the head.
2. The improvement as set forth in claim 1 wherein the alcohol is 70% isopropyl alcohol solution.
3. The improvement as set forth in claim 1 wherein the swabs are interconnected comprising a string.
4. The improvement as set forth in claim 3 wherein a perforated zone is provided between each adjacent alcohol impregnated swab.
5. The improvement as set forth in claim 4 wherein each zone includes an antiwick segment between each swab.
6. The improvement as set forth in claim 3 wherein the string is housed in an accordian fold of interconnected swabs.
7. The improvement as set forth in claim 1 wherein the opening comprises a slit.
8. The improvement as set forth in claim 1 wherein the container includes a lid and hinge means to open and close the lid.
9. The improvement as set forth in claim 1 wherein the means on the table to connect includes guide means and mutually intercooperating tracks on the container for slidable removable interconnection of the container to the table.

* * * * *